(12) United States Patent
Hoeg et al.

(10) Patent No.: US 7,909,756 B2
(45) Date of Patent: Mar. 22, 2011

(54) ILLUMINATION SYSTEM FOR VARIABLE DIRECTION OF VIEW INSTRUMENTS

(75) Inventors: Hans David Hoeg, Arcadia, CA (US); Eric L. Hale, Altadena, CA (US); Nathan Jon Schara, Pasadena, CA (US); John C. Tesar, Tucson, AZ (US)

(73) Assignee: Karl Storz Imaging, Inc., Goleta, CA (US)

( * ) Notice: Subject to any disclaimer, the term of this patent is extended or adjusted under 35 U.S.C. 154(b) by 984 days.

(21) Appl. No.: 11/339,201

(22) Filed: Jan. 25, 2006

(65) Prior Publication Data
US 2006/0256431 A1 Nov. 16, 2006

Related U.S. Application Data

(60) Provisional application No. 60/647,359, filed on Jan. 26, 2005.

(51) Int. Cl.
*A61B 1/06* (2006.01)
(52) U.S. Cl. ......... 600/173; 600/160; 600/176; 359/431
(58) Field of Classification Search .................. 600/109, 600/160, 164, 170, 171, 173–176, 178, 476; 362/572, 574; 359/431, 831; 385/117
See application file for complete search history.

(56) References Cited

U.S. PATENT DOCUMENTS

| | | | |
|---|---|---|---|
| 3,856,000 A | 12/1974 | Chikama | 128/6 |
| 3,880,148 A | 4/1975 | Kanehira et al. | 128/6 |
| 4,697,577 A | 10/1987 | Forkner | 128/6 |
| 5,088,492 A | 2/1992 | Takayama et al. | 128/654 |
| 5,621,830 A | 4/1997 | Lucey et al. | 385/25 |
| 5,700,236 A * | 12/1997 | Sauer et al. | 600/175 |
| 5,762,603 A | 6/1998 | Thompson | 600/112 |
| 5,800,341 A * | 9/1998 | McKenna et al. | 600/109 |
| 6,007,484 A * | 12/1999 | Thompson | 600/173 |
| 6,371,909 B1 * | 4/2002 | Hoeg et al. | 600/173 |
| 6,450,950 B2 * | 9/2002 | Irion | 600/170 |

(Continued)

FOREIGN PATENT DOCUMENTS

DE 201 13 031 1/2002

(Continued)

OTHER PUBLICATIONS

European Search Report; May 26, 2006; 7 pages.

*Primary Examiner* — John P Leubecker
*Assistant Examiner* — Samuel Candler
(74) *Attorney, Agent, or Firm* — St. Onge Steward Johnston & Reens LLC (57) ABSTRACT

A illumination system for variable direction of view instruments is disclosed generally comprising an endoscope having a longitudinal axis and a variable view vector that pivots about a pivot axis angularly offset from the longitudinal axis. The view vector has an attendant viewing field that travels along a path as the view vector pivots, defining a viewing range. A source of illumination is arranged in a plane offset from the plane in which the view vector pivots and provides an annular, solid angle of illumination that covers the viewing range. In certain embodiments, the pivot axis is perpendicular to the longitudinal axis and the illumination plane is parallel to the pivot plane. In some embodiments, the source of illumination is a plurality of light emitting diodes arranged around the pivot axis.

32 Claims, 7 Drawing Sheets

U.S. PATENT DOCUMENTS

| | | | |
|---|---|---|---|
| 6,500,115 B2 | 12/2002 | Krattiger et al. | 600/173 |
| 6,560,013 B1 | 5/2003 | Ramsbottom | 359/431 |
| 6,663,559 B2 | 12/2003 | Hale et al. | 600/118 |
| 6,730,019 B2 * | 5/2004 | Irion | 600/178 |
| 6,916,286 B2 * | 7/2005 | Kazakevich | 600/173 |
| 6,944,316 B2 | 9/2005 | Glukhovsky et al. | 382/107 |
| 7,217,241 B2 * | 5/2007 | Guenier et al. | 600/179 |
| 7,511,733 B2 * | 3/2009 | Takizawa et al. | 348/68 |
| 7,530,948 B2 * | 5/2009 | Seibel et al. | 600/178 |
| 7,578,788 B2 * | 8/2009 | Yokoi et al. | 600/160 |
| 2002/0188177 A1 | 12/2002 | Miyanaga | 600/179 |
| 2003/0092966 A1 * | 5/2003 | Schara et al. | 600/173 |
| 2003/0114730 A1 | 6/2003 | Hale et al. | 600/114 |
| 2004/0210105 A1 | 10/2004 | Hale et al. | 600/101 |

FOREIGN PATENT DOCUMENTS

| | | |
|---|---|---|
| JP | 2002153419 A * | 5/2002 |
| WO | WO 01/22865 | 4/2001 |

* cited by examiner

ILLUMINATION SYSTEM FOR VARIABLE DIRECTION OF VIEW INSTRUMENTS

CROSS-REFERENCE TO RELATED APPLICATIONS

This patent application claims the benefit of, under Title 35, United States Code, Section 119(e), U.S. Provisional Patent Application No. 60/647,359, filed Jan. 26, 2005.

FIELD OF THE INVENTION

The present invention relates to a system for an illumination system for viewing instruments, such as endoscopes. More specifically, the invention relates to a system for illuminating the viewing field in a scope with a variable direction of view.

BACKGROUND OF THE INVENTION

Illumination systems for viewing instruments, such as endoscopes, industrial boroscopes, or other types of scopes, are generally well known in the art. Because the sites being viewed or inspected by such scopes, such as anatomical or industrial cavities, are not naturally illuminated, illumination must first be provided before any useful viewing or image acquisition can take place. Accordingly, a wide array of such systems have been used.

Earlier scopes employed open flames, and later, platinum filaments. Today, most endoscopic illumination is provided via fiber optic channels that receive light from an image guide coupled to an external, high-powered light source, such as a halogen or xenon lamp. Although such fiber optic systems tend to suffer from a number of disadvantages, including some light loss during the transmission from the external source to the tip of the scope, gradual discoloration and loss of transmission efficiency over time, and the breaking of fiber strands, these systems continue to be the most commonly employed method of providing illumination to the viewing site. However, in certain applications, the use of light emitting diodes has emerged as an alternative means for doing so, as described in the imaging systems disclosed in U.S. Pat. No. 6,730,019 to Irion and U.S. Pat. No. 6,944,316 Glukhovsky et al.

Figure 1A:
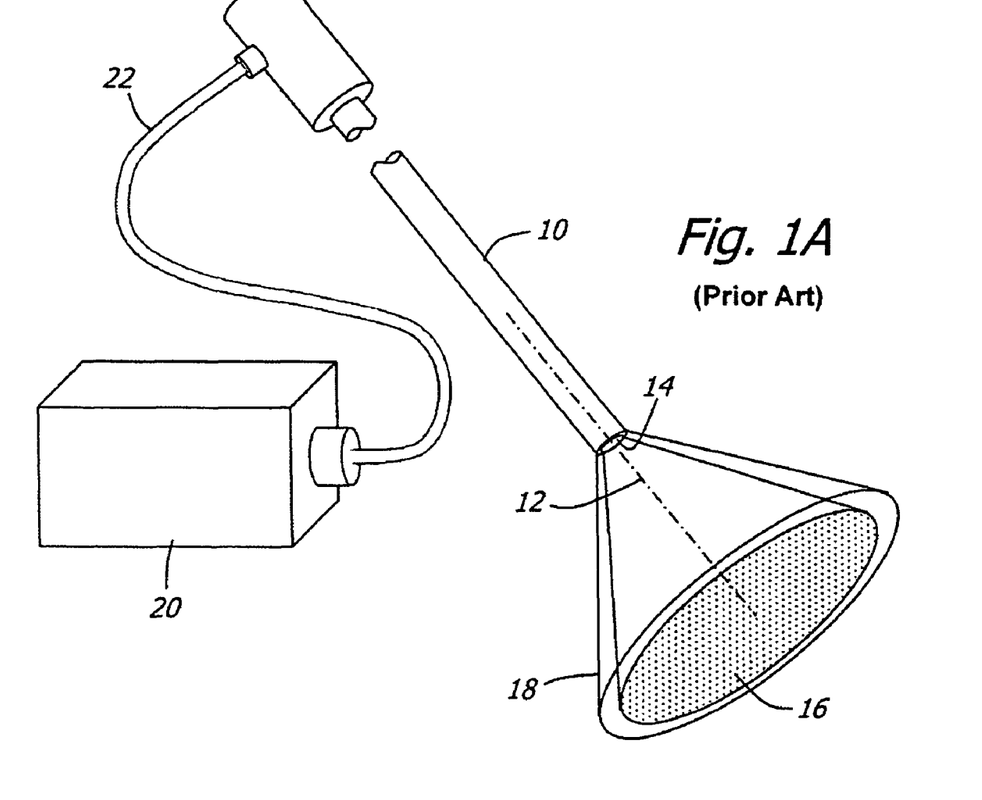
FIGS. 1A-C are schematic views of endoscopic illumination systems existing in the prior art.
Figure 1B:
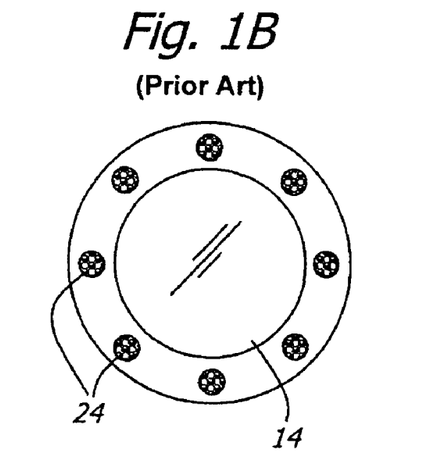
Figure 1C:
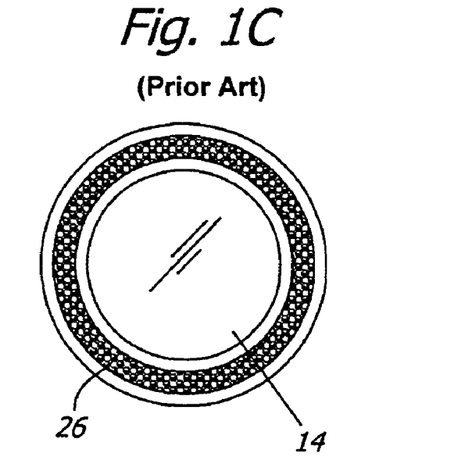

FIG. 1A illustrates a basic illumination system for a traditional endoscope 10. Generally, an endoscope 10 has a fixed line of sight 12 through an objective lens 14. The endoscopic field view field 16 is covered by an illumination field 18, which is typically generated by a remote source 20 and transmitted via a fiber optic light guide 22. The illumination field 18 is designed to cover the entire view field 16 to ensure uniform image brightness. To this end, the illumination field 18 is typically designed to be radially symmetric about the objective lens 14, with light issuing from evenly distributed fiber optic outlets 24, as is shown in FIG. 1B, or a single annular outlet 26, as illustrated in FIG. 1C.

In order to improve the viewing ability of the user, certain endoscopic systems have been provided that include a variable line of sight. Often referred to as swing prism endoscopes, such as that disclosed in U.S. Pat. No. 3,856,000 to Chikama, or pan-tilt endoscopes, such as that described in U.S. Pat. No. 5,762,603 to Thompson, these devices typically have a pivotable line of sight that can cover a certain scanning range. However, with this pivotable line of sight, it becomes necessary to provide illumination over a much wider range than with a single, fixed viewing direction.

Accordingly, a number of illumination systems have been proposed to accommodate these types of endoscopic systems having variable viewing directions. For example, it has been suggested to use separate illumination reflectors, coupled to the imaging reflector, so as to provide a light field that is generally aligned with the viewing field, such as in the systems disclosed in U.S. Pat. No. 3,880,148 to Kanehira et al. and WIPO Publication No. WO 01/22865 to Ramsbottom. However, while this type of arrangement can accommodate a large viewing range, it cannot be made sufficiently compact for midsize (i.e., 4 mm diameter) to small (1 mm diameter) endoscopes.

Another type of system that has been suggested is the use of fibers that are fanned out at the outlet in order to spread the light over the entire viewing range, such as in the systems described in U.S. Pat. No. 4,697,577 to Forkner and U.S. Pat. No. 6,500,115 to Krattiger et al. However, while these arrangements can be made relatively compact, they can only illuminate a limited swing range.

An additional challenge presented by variable direction of view scopes is that, in addition to changing the viewing elevation, it also desirable to be able to rotate the line of sight azimuthally about the shaft of the endoscope in order to achieve truly complete variable viewing. Often, this is accomplished by rotating the entire endoscope. However, this has the disadvantage that the light guide gets wrapped around the instrument in the process. Likewise, endoscopes, that have a fixed handle and a rotatable shaft, allowing the user to perform an azimuthal scan without having to rotate the entire instrument, have a similar problem.

In order to deal with this problem, it has been suggested to use rotating light posts and fiber optic slip rings, such as is described in U.S. Pat. No. 5,621,830 to Lucey et al. However, in practice, these systems have not proven sufficiently effective to replace the standard solution, which entails leaving slack in the fiber bundle in order to give it some freedom to twist. Other systems have been proposed that employ couplings allowing wide azimuthal scanning ranges, such as that disclosed in Krattiger et al. However, these devices employ a mechanism that prevents rotation beyond a particular scan range so that the user does not inadvertently over-twist and destroy the illumination fibers. This limited rotation restricts viewing freedom by forcing the operator to reset the viewing direction once the end of a particular range has been reached.

When the operator decides to change the viewing direction, the instrument should be able to move directly to any new viewing configuration without mechanical constraints or a need to unwind the mechanism and approach the desired view from the opposite direction. Additionally, with the advent of computer-controlled variable direction-of-view endoscopes, such as that disclosed in U.S. Pat. No. 6,663,559 to Hale et al., it has become possible to execute omniramic frame capture sequences for the purpose of building endoscopic maps. Such capture sequences would be most effective and minimize mechanical wear if they are able to be executed in a single continuous scan with no reciprocating motion.

What is desired, therefore, is a system that employs a fixed illumination system that can accommodate the changing line of sight in a scope with a variable direction of view. What is further desired is a system that is both compact and can illuminate a generally circular band swept out by viewing field that moves in accordance with the moving view vector. What is also desired is an illumination system that permits unlimited and continuous rotation of the scope shaft.

SUMMARY OF THE INVENTION

Accordingly, it is an object of the present invention to provide an illumination system for a scope that requires minimal space.

It is a further object of the present invention to provide an illumination system for a scope that can provide illumination in a generally circular band around the pivot axis of the view vector of the scope.

It is yet another object of the present invention to provide an illumination system for a scope that can provide illumination that covers the entire viewing range of the viewing field as the view vector pivots around the view vector.

It is still another object of the present invention to provide an illumination system for a scope that will freely rotate with the scope.

In order to overcome the deficiencies of the prior art and to achieve at least some of the objects and advantages listed, the invention comprises an illumination system for variable direction of view instruments, including an endoscope having a longitudinal axis and a variable view vector with an attendant viewing field, a pivot axis which is angularly offset from the longitudinal axis and about which the view vector pivots in a scan plane, wherein the viewing field moves along a path as the view vector pivots about the pivot axis, a viewing range defined by the path of the viewing field, and a source of illumination arranged in an illumination plane offset from the scan plane that provides an illumination field that covers the viewing range.

In another embodiment, the invention comprises an illumination system for variable direction of view instruments, including an image transmission assembly having a longitudinal axis and a distal end, a viewing element disposed at the distal end of the image transmission assembly, the viewing element having a rotational axis which is angularly offset from the longitudinal axis and about which the viewing element rotates in a first plane, and a source of illumination arranged in a second plane substantially parallel to the first plane.

In yet another embodiment, the invention comprises an illumination system for variable direction of view instruments, including an image transmission assembly having a longitudinal axis and a variable view vector with an attendant viewing field, a pivot axis which is angularly offset from the longitudinal axis and about which the view vector pivots in a scan plane, wherein the viewing field moves along a path as the view vector pivots about the pivot axis, a viewing range defined by the path of the viewing field, and a source of illumination arranged in an illumination plane offset from the scan plane that provides an illumination field that covers the viewing range.

In still another embodiment, the invention comprises an illumination system for variable direction of view instruments, including an instrument shaft including a longitudinal axis and a variable view vector having at least two mechanical degrees of freedom, a pivot axis substantially perpendicular to the longitudinal axis and about which the view vector pivots in a scan plane; and a source of illumination arranged in an illumination plane substantially parallel to the longitudinal axis such that the illumination plane is substantially parallel to the scan plane.

DETAILED DESCRIPTION OF THE INVENTION

The basic system of one embodiment for providing illumination for an endoscope having a variable direction of view and in accordance with the invention are illustrated in FIGS. 2-6. As used in the description and drawings, any terms or illustrations referencing the orientation or movement of parts of the system, such as references to "top," "bottom," "above," "below," "over," "under," "above," "beneath," "on top," "underneath," "up," "down," "upper," "lower," "front," "rear," "back," "forward" and "backward", refer to the objects referenced when in the orientation illustrated in the drawings, which orientation is not necessary for achieving the objects of the invention.

Figure 2:
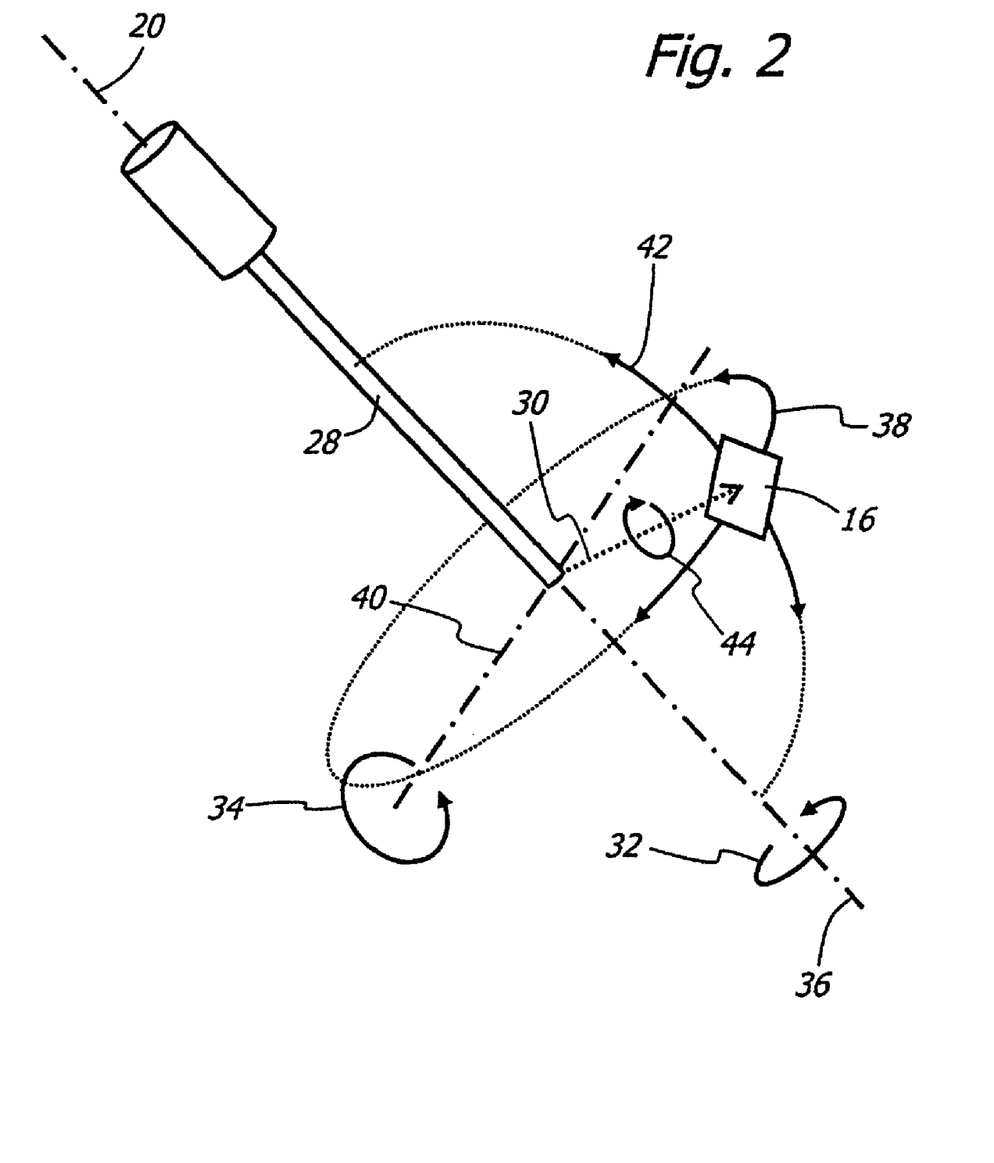
FIG. 2 is a schematic view of the operating principles of a variable direction of view endoscope used with the illumination system of the present invention.

FIG. 2 illustrates the basic operating principles of a variable direction of view endoscope used in accordance with the invention. Such an instrument generally includes a shaft 28 with a longitudinal axis 36. The endoscope has a view vector 30, with an attendant view field 16, with at least two degrees of freedom 32, 34. The first degree of freedom 32 permits rotation of the view vector 30 about the longitudinal axis 36, which allows the view vector 30 to scan in a latitudinal direction 38. The second degree of freedom 34 permits rotation of the view vector 30 about an axis 40 perpendicular to the longitudinal axis 36, which allows the view vector 30 to scan in a longitudinal direction 42. A third degree of freedom 44 may also be available because it is usually possible to adjust the rotational orientation of the endoscopic image.

Figure 3A:
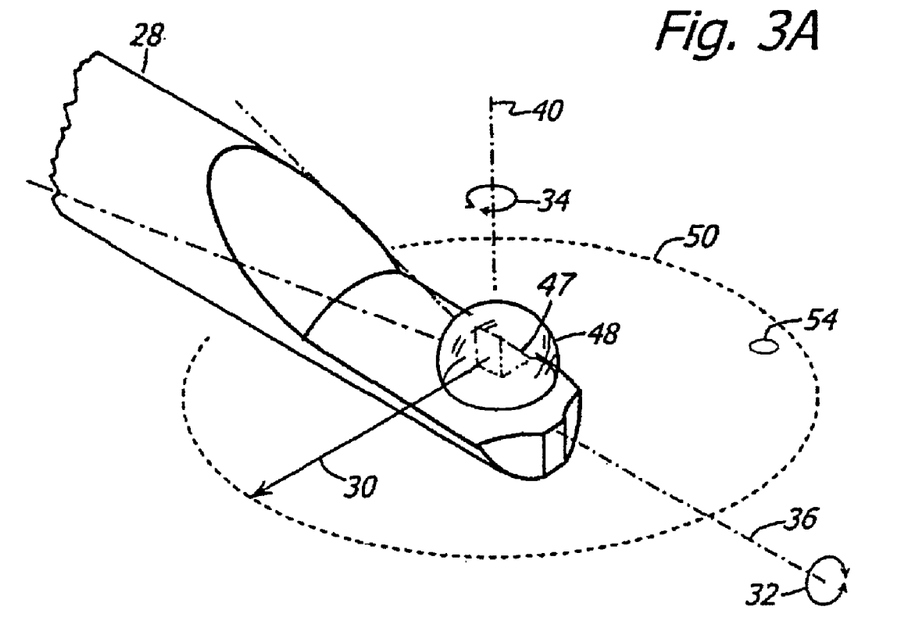
FIG. 3A is a perspective view of the distal end of the endoscope of FIG. 2 illustrating a scan plane thereof.

As shown in FIG. 3A, in certain advantageous embodiments, a right-angled prism 47, housed in a spherical viewing window 48, can rotate about the axis 40, representing the second degree of freedom 34. Accordingly, the view vector 30 sweeps in the longitudinal direction 42, resulting in an effective viewing range 50 in the view vector scan plane 54. With this ability to sweep out such a large range, it is, of course, useful to provide sufficient illumination over the entire range 50.

Figure 3B:
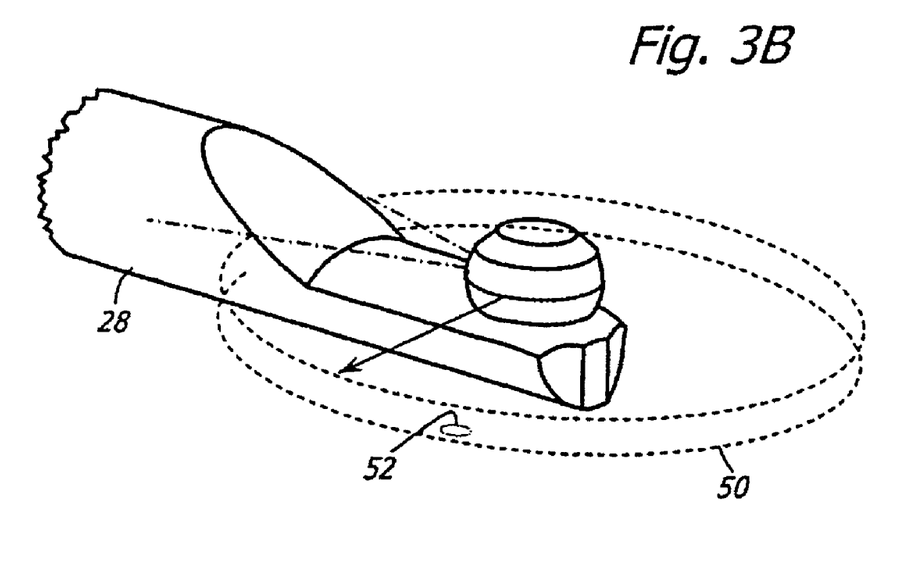
FIG. 3B is a perspective view of the distal end of the endoscope of FIG. 2 illustrating an illumination plane relative to the scan plane.

Because using the same optical conduit as both the illumination and the image guide is not very effective with current optics technology, the illumination outlets/elements are positioned in a different plane 52 than the view vector scan plane 54, as illustrated in FIG. 3B, in order to not block the view field 31. In certain advantageous embodiments, this illumination plane 52 is parallel to the view vector scan plane 54. Generally, it is only necessary to illuminate over the viewing range 50, and not a full spherical solid angle about the endoscope tip, because the illumination plane 52 will rotate with the entire endoscope 28 as it is rotated about its longitudinal axis 36 through the unlimited range of the second degree of freedom 34.

Figure 4A:
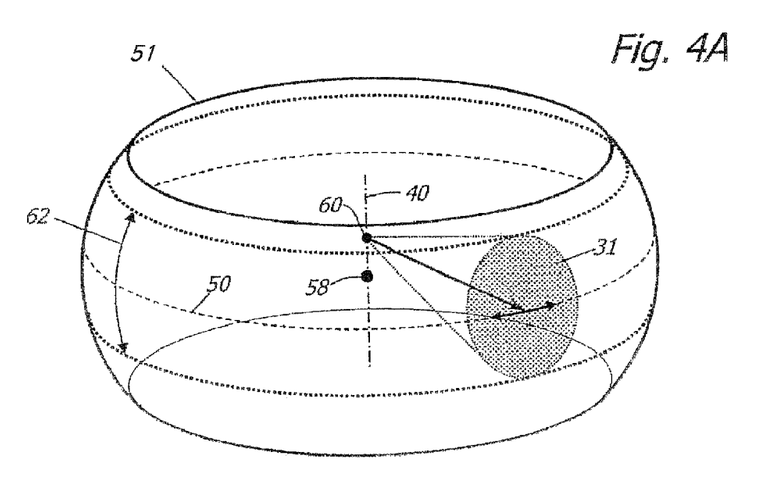
FIG. 4A is a schematic view of a solid angle of illumination and its relation to a viewing range of the endoscope of FIG. 2.

As shown in FIG. 4A, as the view vector 30 is rotated about the pivot axis 40, a viewing range 62 is swept out by the field of view 31 as it travels along the viewing range 50. The illumination outlets/elements positioned in the illumination plane 52 create an illumination field 51, symmetric about the illumination plane 52, represented as an annular solid angle. This field 51 is typically centered on the view vector pivot axis 40, its center 58 being offset from the view vector pivot point 60 along the pivot axis 40. In practice, the precision of this alignment is typically only relevant to the extent that it advances the goal of supplying uniform and consistent illumination intensity to the view field 31 throughout the viewing range 50.

The illumination field 51 is larger than the annular solid angle 62, such that the field 51 completely covers the viewing range 62 that is swept out by the field of view 31 as it travels along a path through the range 50. While the illumination field 51 depicted in FIG. 4A is a complete circular strip, in certain embodiments, as with the endoscope tip configuration shown in FIGS. 3A-B, this is not required, as it is not necessary to illuminate directly backwards (i.e., where the view vector 30 is parallel to the longitudinal axis 36 and pointed at endoscope shaft 28). This is illustrated in the schematic plan view of the near-360° endoscopic illumination system shown in FIG. 4B.

Figure 4B:
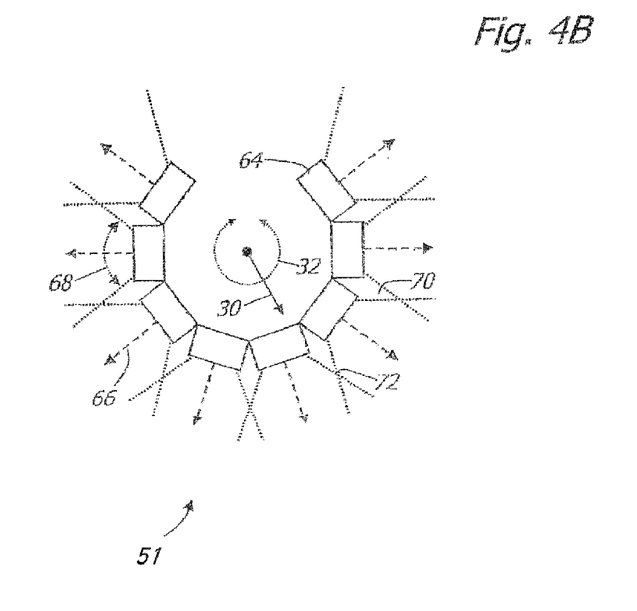
FIG. 4B is a schematic view of an LED arrangement for generating the solid angle of illumination of FIG. 4A.

In certain advantageous embodiments, the illumination elements are light emitting diodes 64, arranged symmetrically around the pivot axis 40. For example, in certain embodiments, eight LEDs are arranged with their emission centerlines 66 substantially perpendicular to the pivot axis 40 and directed such that the illumination field 68 of each LED 64 overlaps with the illumination fields 68 of immediately adjacent LEDs 64, generating a uniformly blended illumination field 51. Due to the discrete nature of such arrangements of illumination elements 64, there may be dark regions 70. However, with advantageous designs, the intersection of adjacent illumination fields 72 will occur closer to the body of the endoscope than the smallest practical imaging distance. Random reflections of light within an enclosed cavity will also practically eliminate such dark regions 70.

Figure 5A:
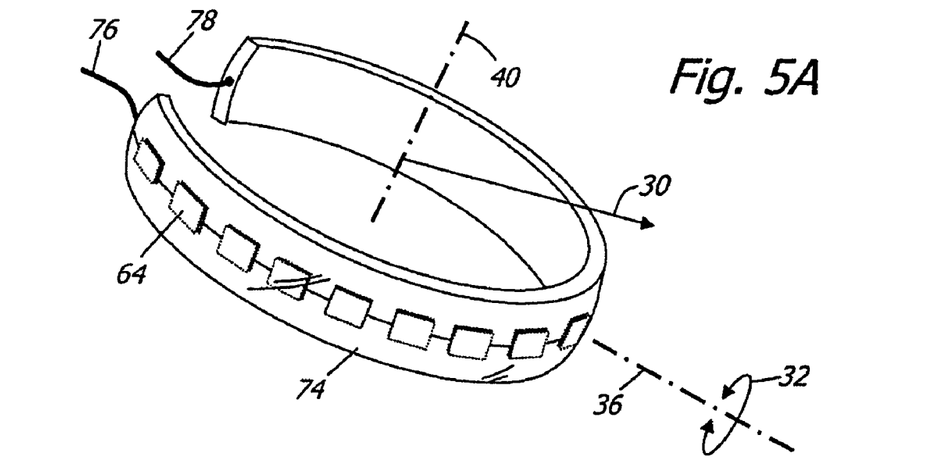
FIG. 5A is a perspective view showing additional detail of the LED arrangement of FIG. 4B.
Figure 5B:
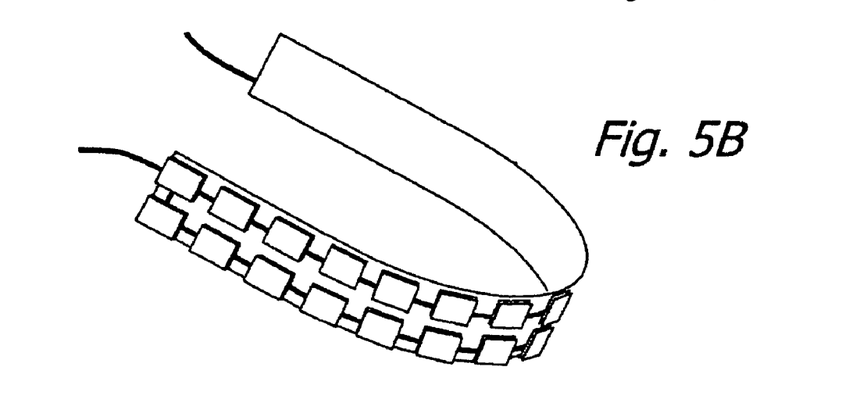
FIG. 5B is a perspective view showing additional detail of the LED arrangement of FIG. 4B.

FIG. 5A illustrates a particular embodiment of a circular LED illumination system. The semiconducting diodes 64 are embedded in an annular, optically clear housing 74. This housing may be made of various materials, such as resin, glass, or plastic, according to design requirements, such as heat dissipation, robustness, light diffusion, or biological toxicity (medical applications) considerations. The LEDs 64 are connected in series, with the ends of the chain being the positive and negative power leads 76, 78. Depending on voltage or current restrictions, the LEDs 64 can also be connected in parallel, which would not fail as the result of the malfunction of a single element, or may, in some embodiments, comprise a combination of series and parallel, as shown in the U-shaped configuration Illustrated in FIG. 5B. The illumination systems shown in FIGS. 5A-B are built as independent modules, which can readily be integrated into an endoscope.

Figure 5C:
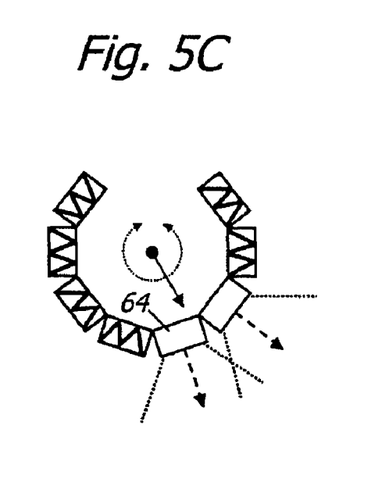
FIG. 5C is a schematic view of the LED arrangement of FIG. 4B illustrating directed illumination for a specific viewing direction.
Figure 5D:
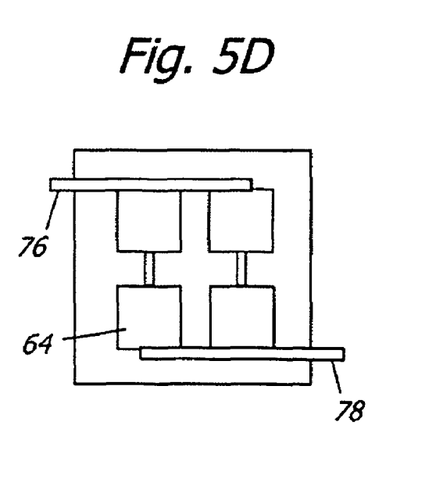
FIG. 5D is a schematic view of a sub-array of the LED arrangement of FIG. 5C.

The view vector 30 and the illumination module rotate about the longitudinal axis 36 as a unit. In some embodiments, each module is built as a set of sub-arrays (at least one LED) with independent power leads. This can simplify manufacturing and assembly, and more importantly, sub-arrays can be selectively activated, such that only elements with principal illumination directions generally aligned with the current view vector orientation are lit at any time, conserving power and heat, as illustrated in FIG. 5C. Accordingly, the system is capable of providing adaptive illumination where the illumination direction is coordinated with the current viewing direction by only activating appropriately aligned LEDs. It also allows for intermittent activation where the elements can be pulsed in synchronization with an electronic imaging system for the purposes of conserving power, minimizing heat production, overdriving the LEDs high intensity flashes (useful for taking high-resolution stills). Moreover, depending on the types of LEDs used and the power supplied, this system is also capable of multispectral illumination and structured lighting with multiple illumination angles. FIG. 5D shows a sub-array of four LEDs 64 connected in a series-parallel combination.

Figure 6A:
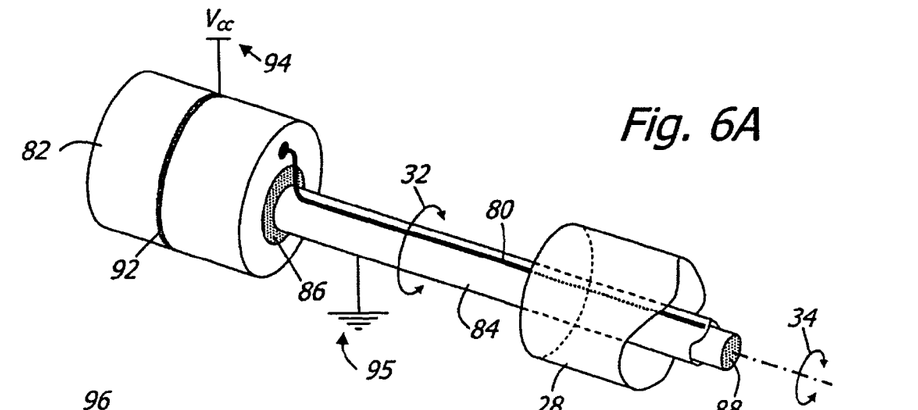
FIGS. 6A-C are schematic views showing additional detail of the power transmission system for supplying power to the LED arrangement of FIG. 4B.

Because part of the purpose of this onboard solid state illumination system is to allow rotation that is not constrained by twist-limited fiber optic systems, it is necessary to implement an electrical slip-ring for transmitting power to the LEDs. FIG. 6A shows an implementation of such a power transmission where a wire 80 carries power (Vcc) from a slip-ring 82, rigidly linked to a sleeve 84 through an insulation layer 86, to a distal illumination system. The wire 80 is in this case mounted to the surface of the sleeve 84, which houses an opto-mechanical transmission shaft 88. In certain embodiments, this transmission shaft 88 serves the dual purpose of relaying the endoscopic image and also transmitting rotational motion (the second degree of freedom) to the distal rotating prism 47. The endoscopic shaft 28 houses the sleeve 84, and these two tubes are rigidly coupled at the tip of the endoscope. When the first degree of freedom 32 is actuated, the shaft 28, sleeve 84, wire 80, and slip-ring 82 rotate. In this version, the illumination system is grounded 95 to the sleeve-shaft assembly.

Figure 6B:
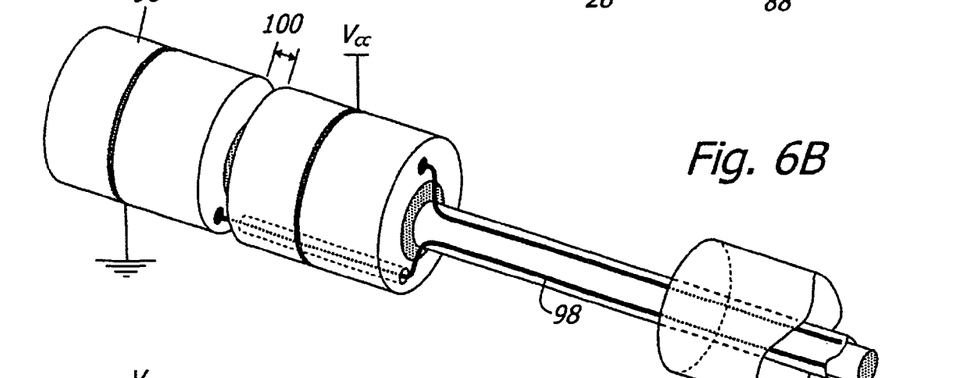
Figure 6C:
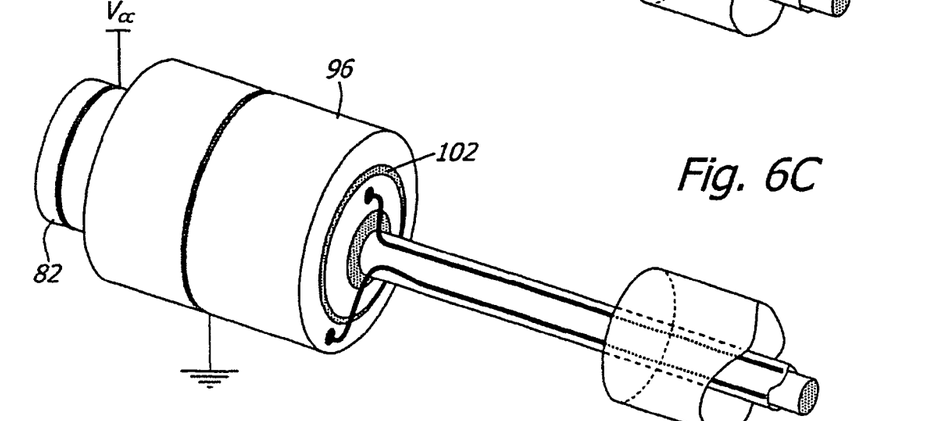

Depending on the electrical safety requirements of the application, it may be desired to use different grounding schemes. FIG. 6B illustrates a designated grounding slip-ring 96 connected to a ground wire 98 of the illumination system and separated from the power slip-ring 82 by an insulating layer of air 100, while FIG. 6C shows a radial arrangement with power and ground slip-rings 82, 96, separated by an additional layer of insulation 102.

Figure 7A:
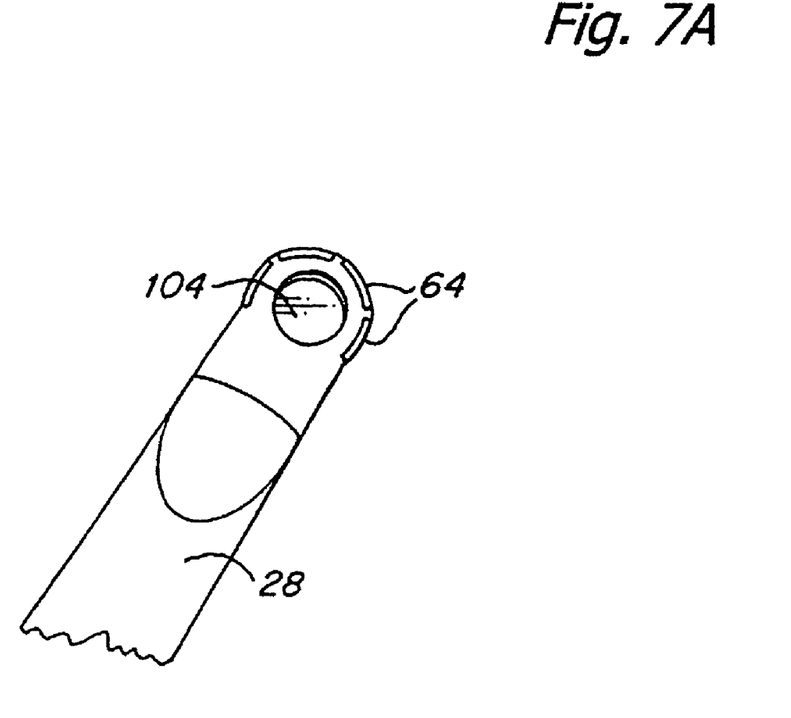
FIGS. 7A-B are perspective views of the distal end of the endoscope of FIG. 2.
Figure 7B:
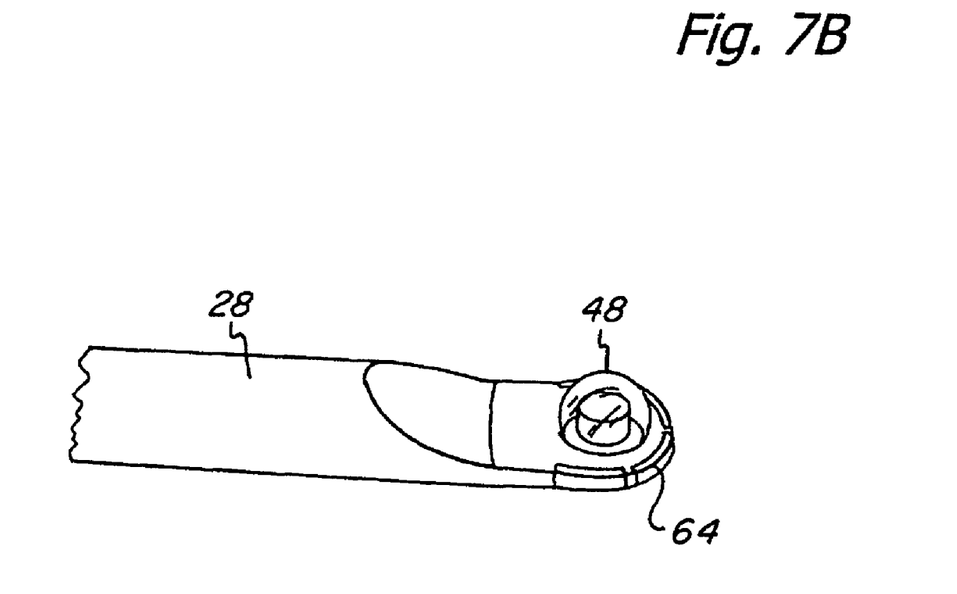

FIG. 7A shows an actual view of the distal end of the endoscope. The endoscope shaft 28 has an empty socket 104 for holding the rotating prism and the spherical viewing window. Four white light LEDs 64 are arranged in a circle around this socket 104. A side view of this tip configuration, illustrated in FIG. 7B, shows the relative positions of the viewing window 48 and the LEDs 64.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. An illumination system for variable direction of view instruments, comprising;
   an instrument shaft having a longitudinal axis and a distal end;
   a viewing element with a view vector disposed at the distal end of said shaft, said viewing element having a pivot axis which is angularly offset from said longitudinal axis and about which said view vector pivots in a scan plane, wherein said view vector has an attendant viewing field, and wherein said viewing field moves along a path as said view vector pivots about the pivot axis;

a viewing range defined by the path of the viewing field; and a source of illumination arranged in an illumination plane offset from the scan plane that provides an illumination field that provides substantially complete coverage of said viewing range;

wherein said viewing element comprises a right-angled prism.

2. The system of claim 1, wherein said pivot axis is substantially perpendicular to said longitudinal axis.

3. The system of claim 1, wherein the illumination plane is substantially parallel to the scan plane.

4. The system of claim 3, further comprising a pivot point at which said view vector pivots about the pivot axis, wherein said illumination field has a center located on said pivot axis and offset from said pivot point.

5. The system of claim 1, wherein said viewing range comprises an annular solid angle defined by the path of the viewing field.

6. The system of claim 5, wherein said illumination field comprises an annular solid angle that is larger than said viewing range annular solid angle.

7. The system of claim 1, wherein the illumination plane rotates with said view vector when said view vector rotates about said longitudinal axis.

8. The system of claim 1, wherein said source of illumination comprises a plurality of illumination elements arranged along the illumination plane.

9. The system of claim 8, wherein said plurality of illumination elements comprises a plurality of light emitting diodes.

10. The system of claim 9, wherein said plurality of light emitting diodes are arranged symmetrically around said pivot axis.

11. The system of claim 10, wherein:
each of said light emitting diodes has an emission centerline that defines an illumination field for that diode; and
said plurality of diodes are arranged such that the emission centerlines of said diodes are substantially perpendicular to said pivot axis.

12. The system of claim 11, wherein said plurality of diodes are arranged such that the illumination field of each diode overlaps with the illumination fields of adjacent diodes.

13. The system of claim 9, further comprising an annular, optically clear housing, wherein said plurality of diodes are arranged in said housing.

14. The system of claim 1, wherein said pivot axis is a first pivot axis and the scan plane is a first scan plane, further comprising a second pivot axis about which said view vector pivots in a second scan plane.

15. The system of claim 14, wherein said second pivot axis is substantially perpendicular to said first pivot axis.

16. The system of claim 1, further comprising:
an electrical slip ring for receiving power from a power source; and
a wire connected to said slip ring and said source of illumination for transmitting power along said shaft to said source of illumination.

17. The system of claim 1, wherein said instrument shaft comprises an endoscope shaft.

18. An illumination system for variable direction of view instruments, comprising:
an image transmission assembly having a longitudinal axis and a distal end;
a viewing element with a view vector disposed at the distal end of said image transmission assembly, said viewing element having a rotational axis which is angularly offset from said longitudinal axis and about which said viewing element rotates so that said view vector pivots in a first plane, wherein said view vector has an attendant viewing field;
a viewing range defined by the path of the viewing field; and
a source of illumination arranged in a second plane substantially parallel to said first plane that provides an illumination field that provides substantially complete coverage of said viewing range;
wherein said viewing element comprises a right-angled prism.

19. The system of claim 18, wherein said rotational axis is substantially perpendicular to said longitudinal axis.

20. The system of claim 18, wherein said source of illumination comprises a plurality of illumination elements arranged along the second plane.

21. The system of claim 20, wherein said plurality of illumination elements comprises a plurality of light emitting diodes.

22. The system of claim 21, wherein said plurality of light emitting diodes are arranged symmetrically around said rotational axis.

23. The system of claim 22, wherein:
each of said light emitting diodes has an emission centerline that defines an illumination field for that diode; and
said plurality of diodes are arranged such that the emission centerlines of said diodes are substantially perpendicular to said rotational axis.

24. The system of claim 23, wherein said plurality of diodes are arranged such that the illumination field of each diode overlaps with the illumination fields of adjacent diodes.

25. The system of claim 21, further comprising an annular, optically clear housing, wherein said plurality of diodes are arranged in said housing.

26. The system of claim 18, further comprising:
an electrical slip ring mounted on said image transmission assembly; and
a wire connected to said slip ring and said source of illumination that transmits power from said slip ring to said source of illumination.

27. The system of claim 26, further comprising a power source electrically connected to said slip ring that supplies power thereto.

28. An illumination system for variable direction of view instruments, comprising;
an image transmission assembly having a longitudinal axis;
said image transmission assembly having a viewing element with a view vector and a pivot axis which is angularly offset from said longitudinal axis and about which said view vector pivots in a scan pivot plane, wherein said view vector has an attendant viewing field, and wherein said viewing field moves along a path as said view vector pivots about said pivot axis;
a viewing range defined by the path of the viewing field; and
a source of illumination arranged in an illumination plane offset from the view vector pivot plane that provides an illumination field that provides substantially complete coverage of said viewing range;
wherein said viewing element comprises a right-angled prism.

29. The system of claim 28, wherein said pivot axis is substantially perpendicular to said longitudinal axis.

30. The system of claim 28, wherein the illumination plane is substantially parallel to the scan plane.

31. An illumination system for variable direction of view instruments, comprising;
- an instrument shaft including a longitudinal axis and a distal end;
- a viewing element with a view vector having at least two mechanical degrees of freedom disposed at the distal end of said shaft, said viewing element having a pivot axis substantially perpendicular to said longitudinal axis and about which said view vector pivots in a scan plane, wherein said view vector has an attendant viewing field, and wherein said viewing field moves along a path as said view vector pivots about said pivot axis;
- a viewing range defined by the path of the viewing field; and
- a source of illumination arranged in an illumination plane substantially parallel to said longitudinal axis such that the illumination plane is substantially parallel to the scan plane and provides an illumination field that provides substantially complete coverage of said viewing range;
- wherein said viewing element comprises a right-angled prism.

32. The system of claim 31, wherein the illumination plane rotates with said view vector when said view vector rotates about said longitudinal axis such that the illumination plane remains parallel with the scan plane.

* * * * *